United States Patent

Sunagawa et al.

Patent Number: 5,216,186
Date of Patent: Jun. 1, 1993

[54] CRYSTALLINE PALLADIUM TETRAKIS(TRIPHENYLPHOSPHINE) AND A PROCESS FOR PREPARING THE SAME

[75] Inventors: Makoto Sunagawa, Hyogo; Haruki Matsumura, Nara; Yutaka Kitamura, Hyogo, all of Japan

[73] Assignee: Sumitomo Pharmaceuticals Co., Ltd., Osaka, Japan

[21] Appl. No.: 810,035

[22] Filed: Dec. 19, 1991

[30] Foreign Application Priority Data

Dec. 20, 1990 [JP] Japan .................. 2-413188
Jun. 20, 1991 [JP] Japan .................. 3-175981

[51] Int. Cl.$^5$ .............................. C07F 15/00
[52] U.S. Cl. ........................ 556/21; 556/136
[58] Field of Search ................... 556/21, 136

[56] References Cited

U.S. PATENT DOCUMENTS 4,945,174  7/1990  Huser et al. .............. 556/21 X
4,994,590  2/1991  Takaya et al. ............. 556/21
5,012,002  4/1991  Kumobayashi et al. ...... 556/21 X

FOREIGN PATENT DOCUMENTS 1338741  11/1973  United Kingdom .

OTHER PUBLICATIONS

D. R. Coulson, "Tetrakis(Triphenylphosphine)Palladium(O)", *Inorganic Synthesis*, vol. 13, pp. 121–124, 1973.

*Primary Examiner*—Arthur C. Prescott
*Attorney, Agent, or Firm*—Sughrue, Mion, Zinn, Macpeak & Seas

[57] ABSTRACT

Crystalline palladium tetrakis (triphenylphosphine) which exhibits a specific powder X-ray pattern and is excellent in storage stability is obtained by allowing palladium chloride to react with triphenylphosphine in aprotic polar solvents, treating the reaction mixture with an aqueous hydrazine solution, collecting the resulting crystals by filtration, washing with alcohols and further washing with hydrocarbon solvents.

4 Claims, No Drawings

CRYSTALLINE PALLADIUM TETRAKIS(TRIPHENYLPHOSPHINE) AND A PROCESS FOR PREPARING THE SAME

The present invention relates to stable crystalline palladium tetrakis (triphenylphosphine) and a process for preparing the same.

Palladium tetrakis (triphenylphosphine) is a compound useful in the field of organic synthesis as catalysts for deprotecting reactions of allyl esters or allyl ethers or allylation reactions of carbon or nitrogen atoms.

There are a few methods for preparing palladium tetrakis (triphenylphosphine). For example, British Patent No. 1338741 teaches a method for preparing palladium tetrakis (triphenylphosphine) having a melting point of 94–96° C. (with decomposition) by allowing palladium chloride to react with triphenylphosphine in aprotic polar solvents, treating the reaction mixture with an aqueous hydrazine solution, collecting the resulting crystals by filtration and finally washing them with an alcohol. Inorganic Synthesis, Vol. 13, pp. 121-124 mentions palladium tetrakis (triphenylphosphine) having a melting point of 116° C. (with decomposition).

However, palladium tetrakis (triphenylphosphine) prepared by the conventional methods looses its activity during leaving it to stand in air, and thus it must be handled quickly. Moreover, it encounters the same problem during the storage even under the nitrogen atmosphere.

It is an object of the present invention to provide stable palladium tetrakis (triphenylphosphine) which is able to be produced, stored and used in an industrial scale and a process for preparing the same.

According to the present inventors, stable crystalline palladium tetrakis (triphenylphosphine) is obtained by washing palladium tetrakis (triphenylphosphine) obtained by the conventional preparation methods with hydrocarbon solvents until alcohols remaining in the palladium tetrakis (triphenylphosphine) are removed.

The present crystalline palladium tetrakis (triphenylphosphine) has a powder X-ray pattern shown in Table 1.

TABLE 1

| d (Lattice distance) | $I/I_1$ (Relative strength) |
| --- | --- |
| 4.42 | strong |
| 10.45 | medium |

In this connection, $I/I_1$ shows relative strength based on 100 of maximum diffraction strength.

According to the present process, crystalline palladium tetrakis (triphenylphosphine) is obtained by allowing palladium chloride to react with triphenylphosphine in aprotic polar solvents, treating the reaction mixture with an aqueous hydrazine solution, collecting the resulting crystals by filtration, washing them with alcohols and further washing with hydrocarbon solvents.

The present invention is now described in detail below.

Raw materials used in the present invention are palladium chloride and triphenylphosphine. An amount of triphenylphosphine to be used should be in a proportion of 4 equivalents or more to palladium chloride without a specific limit for the upper limit. The upper limit may be selected from an economical point of view taking into account of the used amount and the yield. Triphenylphosphine is usually used in the range of 4-10 equivalents, preferably in the range of 5-7 equivalents.

The aprotic polar solvents used in the reaction are selected from dimethylformamide, dimethylacetamide, dimethylsulfoxide or the like, preferably dimethylformamide. An amount of the solvent is enough as long as palladium chloride and triphenylphosphine are sufficiently dissolved under a heating condition. There is no specific upper limit, but the solvent is usually used in an amount of 50-150 times to palladium chloride. The temperature required for the dissolution is selected from the range of from 120° C. to the boiling temperature of the reaction solution, preferably 140-160° C.

Palladium chloride and triphenylphosphine are dissolved by heating in aprotic polar solvents to form a palladium complex. The solution of this palladium complex is maintained at the dissolving temperature for 0.5-1 hour and then cooled gradually over a period of 1-2 hours to a temperature at which the next treatment with hydrazine is performed. To the resulting slurry is added an aqueous hydrazine solution to form palladium tetrakis (triphenylphosphine). The aqueous hydrazine solution is used in a concentration of 20-60%, preferably in the range of 20-25%, and in an amount of 2.5 equivalents or more to palladium chloride, preferably in the range of 3-6 equivalents. The temperature for the treatment with the aqueous hydrazine solution is in the range of 80-140° C., preferably in the range of 80-90° C.

Crystals obtained are then cooled to room temperature and collected by filtration. After the filtration was over, the remaining aprotic polar solvents are removed by thorough washing with alcohols. The alcohols are straight chain or branched alcohols having 1-4 carbon atoms, preferably isopropyl alcohol.

Alcohols remaining, if any, in the crystals after the washing, bring about discoloration of the crystals into brown and loss of activity. Thus, washing with hydrocarbon solvents is conducted in order to sufficiently remove the residual alcohol. The hydrocarbon solvents to be used are saturated hydrocarbons having 5-8 carbon atoms, petroleum benzine and petroleum ether, preferably n-pentane, n-hexane and n-heptane. The solvents are then sufficiently removed by drying under a nitrogen stream, reduced pressure or a combination of the two. Crystalline palladium tetrakis (triphenylphosphine) which shows the powder X-ray pattern in Table 1 and is colored in deep green to yellowish green is obtained.

The crystalline palladium tetrakis (triphenylphosphine) thus obtained is easily handled and is able to store for a long period.

The process for preparing the deep green yellowish green crystalline palladium tetrakis (triphenylphosphine) according to the present invention is described in detail by Examples below, but the scope of the present invention is not limited thereto.

EXAMPLE 1

Palladium chloride (4.85 g) and triphenylphosphine (35.9 g) were added to dimethylformamide (267 g), heated to 140° C. and stirred at the temperature for 1 hour. The mixture was then cooled to 80° C. over a period of 1 hour, and a 25% aqueous hydrazine solution (27.5 g) was dropped cautiously of generation of nitrogen gas. After the mixture was stirred at 80-85° C. for 30 minutes, it was cooled to room temperature. Green crystals obtained were collected by filtration under a nitrogen stream. The crystals were washed twice with isopropyl alcohol (55 g each) and twice with n-heptane (40 g each) and dried under reduced pressure to give deep green crystalline palladium tetrakis (triphenylphosphine) (30 g, 95%).

mp: 128-131° C. (dec.).

Palladium content of the product: Found: 9.2%. Calcd: 9.22%.

The powder X-ray pattern of the product is shown in Table 2.

TABLE 2

| d (Lattice distance) | $I/I_1$ (Relative strength) |
|---|---|
| 4.28 | 8 |
| 4.42 | 100 |
| 9.68 | 7 |
| 10.45 | 24 |

EXAMPLE 2

The procedure was performed in the same manner as in Example 1, except that palladium chloride (10.64 g), triphenylphosphine (94.43 g), dimethylformamide (660 g) and a 25% aqueous hydrazine solution (60.08 g) were used in place of the 4.85 g, 35.9 g, 267 g and 27.5 g, respectively, and washing was conducted with ethanol (120 g, twice) in place of the isopropyl alcohol and with n-hexane (180 g×2) in place of the n-heptane (40 g×2). Deep green crystalline palladium tetrakis (triphenylphosphine) (65.9 g, 95%) was obtained.

COMPARATIVE TEST

The palladium tetrakis (triphenylphosphine) obtained by the method described in British Patent No. 1338741 (GB product) and the compound obtained in Example 1 of the present application (SM product) were stored in a dark place for 1 week, and their activities were compared by the following method.

Allyl p-methoxyphenylacetate (308 mg, 1.5 mM), sodium 2-ethylhexanoate (307 mg, 1.85 mM) and triphenylphosphine (15 mg, 0.06 mM) were stirred in ethyl acetate (5 ml). The aforementioned palladium tetrakis (triphenylphosphine) (17.2 mg, 0.015 mM) was added to the mixture under a nitrogen stream and stirred vigorously at room temperature for 2 hours. 1N-HCl (3 ml) was added under stirring to the mixture and the organic layer was separated. An amount of p-methoxyphenylacetic acid, a product, contained in the organic layer was assayed by liquid chromatography to calculate the conversion. The conversions are shown in Table 3.

TABLE 3

|  | GB product | SM product |
|---|---|---|
| Conversion | 25.5% | 79.9% |

It was found out from the result of Table 3 that the crystalline palladium tetrakis (triphenylphosphine) of the present invention is excellent in storage stability as compared with the conventional product.

We claim:

1. A crystalline palladium tetrakis (triphenylphosphine) which shows a powder X-ray pattern having a strong relative strength ($I/I_1$) at a lattice distance of 4.42 and a medium relative strength ($I/I_1$) at a lattice distance of 10.45.

2. Crystalline palladium tetrakis (triphenylphosphine) according to claim 1, which has a melting point (decomposition) of 128-131° C.

3. A process for preparing crystalline palladium tetrakis (triphenylphosphine) which comprises allowing palladium chloride to react with triphenylphosphine in aprotic polar solvents, treating the reaction mixture with an aqueous hydrazine solution, collecting resulting crystals by filtration, washing them with alcohols and further washing with hydrocarbon solvents.

4. A process according to claim 3, wherein the hydrocarbon solvents are n-pentane, n-hexane or n-heptane.

* * * * *